(12) United States Patent
Brandstetter et al.

(10) Patent No.: US 10,775,384 B2
(45) Date of Patent: Sep. 15, 2020

(54) SENSITIVE DETECTION OF PROTEIN HETEROGENEITY BY USE OF ENZYME CASCADES

(71) Applicant: Sandoz AG, Basel (CH)

(72) Inventors: Hans Brandstetter, Bad Reichenhall (DE); Julia Hollerweger, Bad Reichenhall (DE)

(73) Assignee: Sandoz AG, Basel (CH)

( * ) Notice: Subject to any disclaimer, the term of this patent is extended or adjusted under 35 U.S.C. 154(b) by 230 days.

(21) Appl. No.: 16/073,935

(22) PCT Filed: Feb. 1, 2017

(86) PCT No.: PCT/EP2017/052110
§ 371 (c)(1),
(2) Date: Jul. 30, 2018

(87) PCT Pub. No.: WO2017/134083
PCT Pub. Date: Aug. 10, 2017

(65) Prior Publication Data
US 2019/0041392 A1    Feb. 7, 2019

(30) Foreign Application Priority Data
Feb. 2, 2016    (EP) .................................. 16153751

(51) Int. Cl.
*G01N 33/68* (2006.01)
*C12N 9/10* (2006.01)
*C12N 9/78* (2006.01)
*G01N 33/58* (2006.01)

(52) U.S. Cl.
CPC ....... *G01N 33/6842* (2013.01); *C12N 9/1044* (2013.01); *C12N 9/78* (2013.01); *G01N 33/582* (2013.01); *G01N 33/6803* (2013.01); *C12Y 203/02013* (2013.01); *C12Y 305/03015* (2013.01)

(58) Field of Classification Search
None
See application file for complete search history.

(56) References Cited

FOREIGN PATENT DOCUMENTS

| EP | 2062911 A1 | 5/2009 |
|---|---|---|
| WO | 02077016 A2 | 10/2002 |

OTHER PUBLICATIONS

Dokudovskaya et al. "Protease Accessibility Laddering: A Proteomic Tool for Probing Protein Structure" (Structure 2006 vol. 14, p. 653-660). (Year: 2006).*
Liu et al. (I) "Functional Role of Dimerization of Human Peptidylarginine Deiminase 4 (PAD4)" (PLoSone 2011 vol. 6: e21314). (Year: 2011).*
Liu et al. (II) "Probing the Roles of Calcium-Binding Sites during the Folding of Human Peptidylarginine Deiminase 4" (Scientific Report 2017 vol. 7, p. 2429). (Year: 2017).*
Kanno et al. "Human Peptidylarginine Deiminase Type III: Molecular cloning and Nucleotide Sequence of the cDNA, Properties of the Recombinant Enzyme, and Immunohistochemical Localization in Human Skin" (J. Invest Dermatol. 2000 vol. 115: 813-823). (Year: 2000).*
Arnott, David, et al., ABRF-PRG04: differentiation of protein isoforms, Journal of biomolecular techniques, Apr. 1, 2007, pp. 124-132, Retrieved from the Internet http://ncbi.nlm.nih.gov/pmc/articles/PMC2062542/pdf/jbt-18-124.pdf on Jul. 30, 2018.
Fontana, Angelo, et al., Probing protein structure by limited proteolysis, Acta biochimica Polonica, Jan. 1, 2004, p. 299, Retrieved from the Internet http://actabp.pl/pdf/2_2004/299.pdf on Jul. 30, 2018.
Fontana, Angelo, et al., Probing the Conformational State of Apomyoglobin by Limited Proteolysis, J. Mol. Biol., 1997, vol. 266, No. 2, pp. 223-230.
International Search Report and Written Opinion for PCT/EP2017/052110, dated Aug. 10, 2017, 11 pages.

* cited by examiner

Primary Examiner — Changhwa J Cheu
(74) Attorney, Agent, or Firm — Luedeka Neely Group, P.C.

(57) ABSTRACT

The present invention deals with a method for detecting a protein in a protein sample by amplifying and enhancing small differences between proteins contained in the protein sample. In particular, the present invention uses a cascade of enzymatic modification steps to detect and identify a protein in a protein sample by enhancing small differences between the protein and other proteins contained in the protein sample. Further, the present invention provides a method for distinguishing two proteins having substantially identical or similar amino acid sequences but different protein conformations.

12 Claims, 7 Drawing Sheets

SENSITIVE DETECTION OF PROTEIN HETEROGENEITY BY USE OF ENZYME CASCADES

This application is a Section 371 national phase entry of PCT application PCT/EP2017/052110, filed Feb. 1, 2017. This application also claims the benefit of the earlier filing date of European patent application 16153751.9, filed Feb. 2, 2016.

The present invention deals with a method for detecting a protein in a protein sample by amplifying and enhancing small differences between proteins contained in the protein sample. In particular, the present invention uses a cascade of enzymatic modification steps to detect and identify a protein in a protein sample by enhancing small differences between the protein and other proteins contained in the protein sample. Further, the present invention provides a method for distinguishing two proteins having identical or similar amino acid sequences but different protein conformations.

BACKGROUND OF THE INVENTION

Contrasting small molecules, proteins are not only defined by their chemical formula. Specifically, while the identity of a small molecule can be often confirmed by mass spectrometric methods, conformational richness in proteins is critical for their function. Even small conformational changes that can be triggered by differences in pH can completely revert the enzymatic properties of a protein, as exemplified by the protease and ligase activity of legumain (Dail E. et al., "*Structure and mechanism of an aspartimide-dependent Peptide ligase in human legumain*", Angew. Chem. Int. Ed. Engl. (2015), 54(1), 2917-21).

Given the intimate relation of protein structure and function, the exact knowledge of variations in protein structure is of utmost importance in particular for proteins that are therapeutically or diagnostically used. Lack-of-function changes may render a given therapeutic protein less active, which often can be compensated by an adjusted dosage; gain-of-function changes are often causing severe side effects. Typical gain-of-function changes are immune reactions which may lead to the generation of antibodies. These antibodies may neutralize the therapeutic agent, acting as inhibitors. Even worse, the immune reactions may mount to a severe inflammatory response, e.g. to a "cytokine storm". In case of such an immune reaction, all related protein therapies may become inapplicable due to the cross-reactivity of the immune reaction. Furthermore, endogenous proteins that are homologous to the therapeutic agent are likely to be recognized by the triggered immune response as well, with possibly disastrous consequences.

In consequence, there is an increasing need in the art for detecting conformational changes in proteins and identifying proteins differing from other proteins only by their conformation, even though they may have sequence identity. In particular, it becomes of utmost importance to gain information about the protein structure and conformation of a protein of interest even from complex protein samples, which requires highly sensitive analytical methods. Further, the detection and identification of proteins differing from a reference protein only by minor conformational changes or posttranslational modifications is of utmost importance in the production and quality management of biosimilar products. In particular, the comparison of a similar biotherapeutic product and its reference biotherapeutic product plays a pivotal role in the assessment for overall biosimilarity.

Mass spectrometry is the work horse of protein analytics in academia and industry alike. Technological improvements allow the analysis of ever more complex protein samples and particularly extend the accessible mass range of the protein samples. Both top-down and bottom-up are typically used for protein identification. However, by the nature of this approach, conformational information on the target protein is hardly accessible. Thus, mass spectrometry is only of limited use when trying to detect small heterogeneities, such as small conformational differences, between proteins. Limited and indirect conformational information can only be obtained by laborious hydrogen-deuterium exchange experiments or the identification of disulphide bonds.

Mass spectrometric analysis is often complemented by an array of spectroscopic analytical techniques, including circular dichroism (CD), Fourier-Transform Infrared spectroscopy (FT-IR), NMR, or more specialized techniques like electron spin resonance or Mössbauer spectroscopy. These spectroscopic techniques may provide conformational information on the target protein, albeit at relatively low resolution. X-ray diffraction may be employed to obtain high resolution (atomic) information on protein structures. However, crystallization is challenging and not always successful, in particular with complex or heterogeneous protein samples. Furthermore, crystallization represents a selection process which bears the intrinsic risk to exclude protein species/conformations which may be functionally important.

New approaches have been reported that employ limited proteolysis (LiP) as a tool to sample the conformation of a target protein in solution.

Feng et al., "*Global analysis of protein structural changes in complex proteomes*", Nature Biotechnology (2014), 10, 1036-1044, describes a method that enables probing of structural transitions of proteins in complex biological environments on a large scale by coupling limited proteolysis to generate small peptides amenable to bottom-up proteomic analysis by LC-MS/MS. However, as acknowledged by the authors, the method lacks sufficient sensitivity to access low-abundance proteins and identification of LiP peptides from such low-abundance proteins will require the addition of appropriate sample-enrichment steps.

Lomenich et al., "*Identification of Direct Protein Targets of Small Molecules*", ACS Chemical Biology (2010), 6(1), 34-46, describes a method for small-molecule target identification referred to as "DARTS" (Drug Affinity Responsive Target Stability). The method relies on drug-protein interactions based on the idea that the presence of a drug stabilizes the structure of its target protein, which results in increased protease resistance. In the DARTS method protein lysates are incubated with the native drug and then treated with proteases. The target proteins are negatively enriched due to their drug-induced protease resistance while non-target proteins fall victim to proteolysis. However, the method generally lacks sufficient sensitivity for the target protein which could either be insufficiently abundant or its enrichment could be masked by other proteins in the sample.

Technical Problem of the Invention

In view of the above, there is an increasing need in the art for new analytical methods which enable the detection and identification of proteins differing from other proteins solely or mainly by their conformational structure, such as the three dimensional (3 D) structure. Further, the method should overcome the prior art problems of low sensitivity and should be easy to perform even without the need for large and expensive equipment.

SUMMARY OF THE INVENTION

The inventors have surprisingly found that a systematic analysis of diverse enzymatic modifications may be used to explore the conformational space of a target protein and discovered that a sequential enzymatic modification of a target protein, referred to in the following as enzyme cascade, is able to dramatically amplify initially small differences between two proteins, enabling their supersensitive detection. The enzyme cascade-amplified signal can then be read out by conventional analytical and functional methods.

The present invention is thus directed to a method for identification of a protein according to claim 1, the method comprising the steps of:
- a) providing a first protein sample comprising at least a first protein,
- b) providing at least a second protein sample comprising at least a second protein having substantially the same amino acid sequence as the first protein but being different from the first protein,
- c) subjecting the at least first and second protein samples to enzymatic modification with a first enzyme having a different binding affinity ($K_M$) and/or catalytic turnover ($k_{cat}$) of the at least first and second protein,
- d) repeating step c) one or more times with a second or further enzyme, wherein each enzymatic modification step amplifies differences between the first and the second protein,
- e1) visualizing differences between the first and second protein,
- e2) optionally quantifying differences between the first and second protein, and
- f) identifying the protein based on visualized and optionally quantified differences between the first and the second protein.

Preferred embodiments of the invention are the subject-matter of dependent claims.

DETAILED DESCRIPTION OF THE INVENTION

The present invention is directed to a method for detecting and identifying a protein on the basis of often minute differences with respect to e.g. composition, posttranslational modification or conformation compared with a protein having substantially the same amino acid sequence. In particular, it has been found out by the inventors that slight conformational differences of otherwise similar or identical proteins can be enhanced and amplified by subjecting the proteins to a sequence of enzymatic modification steps, referred to herein as "enzyme cascade treatment" or, in short, "enzyme cascade" or "cascade treatment". The differences can then be visualized and the target protein identified by various analytical and functional assays.

In the context of the present invention, the terms "detection"/"detecting" and "identification"/"identifying" are used interchangeably.

Figure 1:
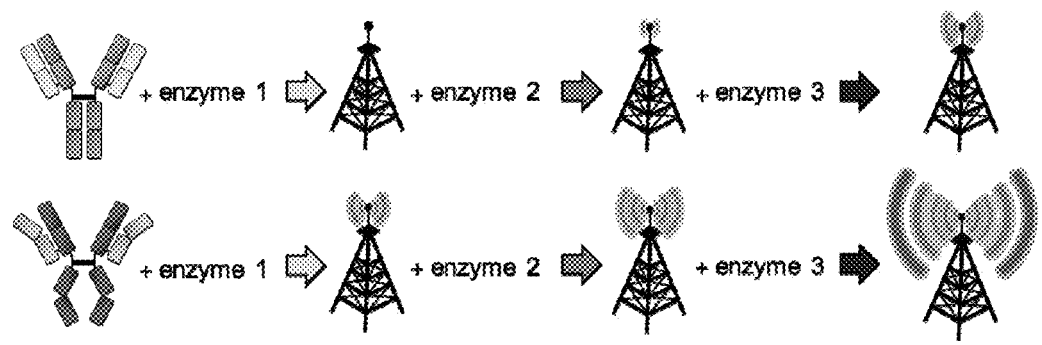
FIG. 1: Schematic illustration of the signal amplification principle by enzyme cascades according to the invention.

FIG. 1 schematically illustrates the amplification of initially small differences between conformational variants of a target protein by the use of enzyme cascades. With each step in an enzyme cascade, target proteins become more different than they were in the beginning, since a distinct amount of enzymatic modifications is introduced due to exposure/non-exposure of different modification sites to the respective attacking enzyme.

First and Second Proteins have Conformational Differences

Steps a) and b) of the method of the present invention comprise the provision of at least a first and second protein, which have substantially the same or identical amino acid sequence despite being different from another, in particular having co- or posttranslational modifications in their chemical composition or exclusively conformational differences with identical composition.

The term "substantially" means that the amino acid sequence of two proteins differs from each other only in five or less amino acids, preferentially two or less amino acids, and more preferably differ only in a single amino acid. In particular, protein structural changes may stem from single nucleotide mutations, which may alter the amino acid sequence only in a single amino acid. Such mutations, however, may have a drastic impact not only on the function and activity of the protein, but may also affect protein structure. Further, one or more asparagine residues of a protein of interest might be subjected to deamidation, changing one or more asparagine residues into aspartate residues. Such deamidation can also greatly affect protein conformation and function. Alternatively, the first and second proteins may differ in the presence or absence of the N-terminal amino acid, such as in the absence or presence of methionine encoded by the start codon of the encoding gene sequence.

In another alternative embodiment, the first and second proteins have amino acid sequences, which are encoded by the same gene. It is noted that despite being encoded by the same gene, and being identical in the encoded amino acid sequence, two proteins may nevertheless be subject to differential posttranslational modifications in the cell. Posttranslational modifications include, without being limited thereto, glycosylation, formation of disulfide bridges, oxidation, acetylation, and the like. Hence, the proteins may include slight structural differences resulting from differential posttranslational modifications, which can be detected by the method of the present invention. Detection of posttranslationally modified but otherwise substantially identical proteins could be of particular importance in case the protein is an antibody, such as a monoclonal antibody. In particular, these posttranslational modifications may lead to conformational changes in the protein structure. Thus, the first and second protein may differ from each other, for example, by one or more of the state of glycosylation, oxidation, acetylation, and disulfide bond formation.

Hence, in another preferred embodiment, the term "substantially the same" means that the first and second proteins are encoded by the same gene. Therefore, the method of the present invention enables the distinction of a protein from another protein even though they may be encoded by the same gene.

In another preferred embodiment, the first and second proteins differ from each other only in their structural conformation, such as their specific 3 D structure, although being encoded by the same gene and/or having the same amino acid sequence. Such conformational differences may result from ligand binding, interaction with other proteins, chemical derivatization or environmental changes, including changes in pH, or changes in the concentration of specific metabolites. For example, an active protein might become inactivated due to a change in temperature, by pH, oxidation, or presence or binding of inhibitors. The inactive form might then differ from the active form only in the protein structure of the otherwise identical protein. The method of the present invention allows detecting the presence or absence of such active or inactive form even in a complex protein sample.

The at least first and second proteins are typically present in different protein samples, such as for example samples taken from different subjects (e.g. human or animal patients), samples being treated or being stored differently, product batches, or samples for structural characterization of a reference and a biosimilar product, such as a reference and biosimilar biopharmaceutical product, or the like, and which are subjected in the method of the present invention to the enzymatic treatments as described herein.

Moreover, one or more of the at least first and second protein samples may be a reference protein sample, which is subjected to the same enzymatic treatment as the (possibly complex) protein sample to be analysed. In such an embodiment, the reference sample may be used for comparison purposes only.

For example, a protein sample to be analysed for the presence or absence of a protein of interest may be subjected to the enzyme cascade treatment of the present invention, and then compared to a reference sample, wherein the reference sample is treated in the same manner as the protein sample to be analysed. Therefore, the enzyme cascade treatment of the at least first and second protein sample does not necessarily have to be carried out simultaneously, but may also be carried out sequentially. In particular, a reference sample may be subjected to the enzyme cascade treatment of the present invention and then stored for (repeated) comparison purposes.

In one particular embodiment, in which the enzyme cascade treatment is used to quantitatively detect the presence of a specific protein, the one or more reference samples may for example be a dilution series of a protein of interest.

A preferred embodiment of the present invention is to distinguish between a biosimilar probe and a reference probe of a biopharmaceutical product. For example, modification of a protein, such as glycosylation of an antibody, may have an impact on the functionality of the protein. In a more specific example, glycosylation of the Fc domain in an IgG1 type monoclonal antibody may have an impact on the Fc functionality and is therefore relevant for antibody function. It may thus be important to distinguish between glyco-iso forms of otherwise identical proteins.

The present invention now provides the possibility to qualitatively or quantitatively determine whether a (complex) protein sample contains the protein in a particular state, such as a specific three dimensional conformation or a glycosylated or non-glycosylated state, by subjecting the protein sample to the enzyme cascade treatment and to then compare it to a reference sample treated in the same way.

Enzyme Cascade Treatment

Steps c) and d) relate to the enzyme cascade treatment and include the step c) of subjecting the at least first and second protein samples to enzymatic modification with a first enzyme having a different binding affinity ($K_M$) and/or catalytic turnover ($k_{cat}$) of the at least first and second protein, and step d) of repeating step c) one or more times with a second or further enzyme, wherein each enzymatic modification step amplifies differences between the first and the second protein.

The Michaelis-Menten constant $K_M$ is typically defined as the substrate concentration at which the reaction rate is half of $V_{max}$, wherein, $V_{max}$ represents the maximum rate achieved by the system at maximum (saturating) substrate concentrations.

The catalytic turnover number $k_{cat}$ is typically defined as the maximum number of chemical conversions of substrate molecules per second that the enzyme will execute for a given enzyme concentration.

In contrast with prior art methods, which conventionally visualize any conformational differences between two protein samples directly after a single enzymatic treatment step, such as limited proteolysis, the inventors have surprisingly found out that heterogeneities present in two or more protein samples may be enhanced and amplified by an enzymatic cascade treatment, which involves two or more enzymatic modification steps.

The enzymes used for the enzymatic modifications are not particularly limited and include all enzymes which can modify a protein provided that the enzyme has the capability to distinguish between the at least first and second protein despite the similarities or identity in the protein's amino acid sequences. The capability to distinguish between two substantially identical proteins differing solely or mainly in their three dimensional conformation may for example result from the sterical or chemical inaccessibility of the enzymatic points of attack, such as the accessibility of the substrate to the enzyme's active sites. Resulting from the conformational differences, the at least first and second proteins are thus differentially modified by the same enzyme, for example due to differences in the number of accessible points of enzymatic attacks. Further, due to the conformational differences, characteristic kinetic properties such as $k_{cat}$ or $K_M$ may vary for the same enzyme between the at least first and second proteins as substrate.

For example, the affinity, i.e. substrate affinity, of binding the first and second protein may be different for the respective modifying enzyme. In consequence, the products resulting from the enzymatic modification differ between the at least first and second protein despite being subjected to the same enzymatic treatment. Further, substrate specificity of an enzyme arises from the three-dimensional structure of the enzyme's active site, which is complementary to the transition state of the reaction. Hence, even small conformational differences between two proteins might effect affinity of substrate binding, i.e. even small conformational differences may effect whether the enzyme binds a substrate or not. In other words, each modification step alters differences between the first and second protein, for example the accessibility of the substrate to the enzyme's active sites or alters the substrate affinity for the first and second protein. Hence, as the modifying enzyme reacts differently with the first and second protein, for example due to their conformational differences, likewise the reaction's products of the enzymatic reactions are different, thereby increasing the differences between the two proteins.

In consequence, the initially small, i.e. conformational, differences are enhanced and amplified by the first enzymatic modification step.

The at least first and second proteins are then subjected to at least a second enzymatic modification step, which differs from the first enzymatic modification step, for example by using a different enzyme. Hence, preferably each enzyme used in an enzymatic modification step is different from any enzyme in the one or more preceding enzymatic modification steps.

The use of two or more different enzymatic modification steps amplifies the initially small differences between the first and second proteins. In consequence, the initially small, i.e. conformational, differences are further enhanced and amplified by each enzymatic modification step.

In a preferred embodiment, the use of two or more different enzymatic modification steps drastically amplifies the initially small differences between the first and second proteins following a power law.

The number of enzymatic modification steps is not particularly limited and depends, inter alia, on the sensitivity of the visualization and detection step. Typically, two or three enzymatic modification steps will be sufficient to amplify a detection signal for allowing the sensitive detection and identification of a protein of interest.

Therefore, in a preferred embodiment, the enzyme cascade treatment consists of two or three, preferably of three, enzymatic modifications. However, the method of the present invention may also encompass four, five or more enzymatic modification steps, provided that each step allows amplification of differences between the first and second proteins, as may be determined by quantification of a detection signal in an analytical assay.

The choice of the used enzyme for the enzymatic modification in step c) and d) is not particularly restricted. A large variety of distinct protein modifications have been reported and may be adapted to the method of the present invention. Among them are protein (de-)phosphorylation; (de-)glycosylation; limited proteolysis (LiP); disulfide formation; diverse oxidation, in particular of sulphur containing amino acids, such as cysteine and methionine; (de-)amidation, in particular of glutamine and asparagine; (de-)imination, aspartate to isoaspartate conversion; (de-)methylation, in particular of (iso-)aspartate; transglutamination; lysine cross-linkage; hydroxylation; acetylation; racemization; ubiquination, and pyroglutamate formation; among others.

Suitable enzymes for performing the enzymatic modification steps may thus be selected, without being limited thereto, from cyclases, such as glutaminyl cyclases; phosphatases; kinases; methyl transferases, such as isoaspartate methyl transferases; ligases; proteases; oxidases; hydroxylases; reductases; isomerases; ubiquitinases; acetylases; transglutaminases; and deiminases.

Proteases may be selected from the class of serine proteases, cysteine proteases, aspartate proteases, threonine proteases, glutamic acid proteases, or metalloproteases, without being limited thereto. Preferably, the protease is selected from legumain, thrombin, factor Xa papain, pepsin, and the like, depending on the protein of interest, and in particular on the number and accessibility of the cleavage sites.

Preferably, the protease used for enzymatic modification is an enzyme used for limited proteolysis (LiP). LiP involves the use of either proteases with narrow substrate specificity or broad-specificity proteases under controlled reaction conditions, such that initial cleavage sites are dictated by the structural features of the protein, as described for example by Fontana et al., "*Probing protein structure by limited proteolysis*", Acta Biochim. Pol., (2004), 51, 299-321. Most preferably, the protease is legumain, thrombin or factor Xa.

In case of using a protease for enzymatic modification, the protein to be modified is typically cleaved into protein fragments or even peptides, which may remain linked together by covalent or non-covalent interactions. Hence, each subsequent enzymatic modification step following a protease treatment is then imposed to the fragments resulting from proteolytic cleavage. Similarly to this, likewise the use of other enzymes used for enzymatic modification, such as the use of oxidoreductases for cleavage of disulfide bonds, may lead to the disintegration of the protein of interest. In consequence, step d) of the method of the present invention also encompasses enzymatic modification of fragments of the at least first and second proteins, such as in case of using enzymes leading to cleavage or disintegration of the proteins in one of the preceding enzymatic modification steps.

In a preferred embodiment of the method of the present invention, enzymatic modification is performed by two or more of citrullination (arginine deimination), transglutamination, and proteolysis, and more preferably involves modification performed by citrullination, transglutamination, and protease cleavage. Protease cleavage is preferably performed by limited proteolysis as described above.

In a further preferred embodiment, the first enzyme is peptidyl arginine deiminase, the second enzyme is a protease and the third enzyme is microbial transglutaminase. Alternatively, the first enzyme is a protease, the second enzyme is a peptidyl arginine deiminase and the third enzyme is microbial transglutaminase.

The specific sequence in which modifying enzymes are applied is not particularly restricted, but may be evaluated for optimal signal enhancement. In order to minimize random signals ("noise") and maximize the differences between proteins of interest ("signal"), gentle enzymes are preferred at the first step of the cascade. "Gentle" implies that the enzymatic modification only weakly impacts the integrity of the protein. For example, citrullination may break a salt bridge of an arginine with an aspartate or glutamate residue, whereas the covalent bonds within the protein remain intact. Hence, the integrity of the protein is only gently influenced. In contrast, hydrolysis of a peptide bond, such as by proteolytic cleavage, may lead to the fragmentation of the protein into two or more fragments; hence, the integrity is greatly affected. In consequence, citrullination is preferably used as the first enzymatic modification step, whereas proteolytic cleavage is preferred as a second or further step of the cascade treatment.

Transglutamination allows for the labelling of accessible protein-derived glutamine or lysine residues with synthetic peptides containing a lysine or glutamine, respectively, thus further enhancing differences in the conformation of the protein probes. Moreover, transglutamination is typically preferred as last modification step because in addition to its modifying properties, it further allows the introduction of a label for sensitive signal detection of the cascade-modified protein, such as a chemiluminescent or fluorescent label. Given these considerations, the preferred cascade sequence may be citrullination (peptidyl arginine deiminase, PAD) as the first enzymatic modification step in the cascade, followed by proteolytic cleavage (e.g. by legumain, papain, or pepsin), followed by microbial transglutaminase (mTGase) treatment as a final step.

Signal Detection and Protein Identification

Steps e) and f) of the method of the present invention refer to the readout of the cascades, i.e. to signal detection and protein identification. Step e) comprises visualizing differences between the first and second protein, which is typically achieved by comparing the first and second protein samples after being subjected to the enzyme cascade treatment. Step f) comprises identifying the protein based on visualized differences between the first and the second protein.

The methods that may be used for visualizing the amplified differences between the first and second proteins in step e) include, without being limited thereto, any spectroscopic and chromatographic methods typically used in the art. Such methods are in particular selected from one or more of polyacrylamide gel electrophoresis (PAGE), such as 1D or 2D PAGE methods, Western Blot, ELISA, HPLC, mass spectrometry (MS), such as LC-MS, MALDI-MS or ESI-MS, capillary electrophoreses, Fourier-Transform infrared spectroscopy (FT-IS), circular dichroism (CD), Dynamic light scattering (DLS), thermal shift assay, NMR, X-ray crystallography, chromatography, and fluorescence spectroscopy. In particular, combinations of one or more of these methods may be used for visualization of amplified differences, i.e. signal detection.

Preferably, the method of the present invention comprises the step of labelling the protein with a suitable label, such as a qualitatively or quantitatively detectable label, e.g., a chemiluminescent or fluorescent label. In a preferred embodiment, tag labelling is performed in the final modification step, for example by transglutaminase modification, but may also be performed in step e). Protein labelling may be conventionally performed by labelling the protein of interest with one or more tags selected from biotin, streptavidin, HIS, fluorescent tags, PEG or whole protein tags, such as GFP, MBP or GST, Flag-tag, and Myc-tag.

Signal detection by a method as described above in particular allows quantification of a signal and thus may be used to evaluate whether a specific enzymatic modification step leads to an enhanced differential signal by amplifying differences between a first and second protein. Quantitative detection of the amplified signal may alternatively be performed functionally, for example by binding kinetics analysis of the modified proteins with a ligand (Surface Acoustic Wave, SAW method), as described for example in Lange et al., "*Surface Acoustic Wave (SAW) biosensors: coupling of sensing layers and measurement*", Methods Mol. Biol. (2013), 949, 491-505, or other analytical methods to quantify protein interaction such as Surface Plasmon Resonance (SPR), thermophoresis, isothermal microcalorimetry (ITC).

Steps e) and f) of visualizing differences between the first and second protein and identifying the protein based on visualized differences between the first and the second protein further allows to determine the statistical significance and reproducibility of protein heterogeneities in the method of the present invention. This may be achieved for example by quantitative enzyme cascade readout.

In a preferred embodiment, the protein samples are being labeled, such as with a synthetic peptide carrying a fluorophore or a biotin, which may be achieved by a terminal transglutamination reaction. The presence of such label(s) allows for quantification either by direct processes, such as measuring the fluorescence of a fluorophore, or indirect processes, such as by performing an immunoblot, in which a labelling intensity can be determined as a function of a molecular mass of a protein.

In particular, an immunoblot may be considered as representing a function x(i) relating to the labeling intensity x (e.g., the number of biotin labels) to the corresponding molecular mass i. Different sample treatments may then result in different labeling intensity distributions, x(i), y(i).

The modification of the protein samples can then be evaluated by using a Pearson product correlation function (r), which can further be interpreted as the approximate % identity $r^2$ (or complementary % deviation, $1-r^2$. Complementary, relative differences of the labelling intensities x at a given mass i, $<|x_i-y_i|>/<|x_i|>$, quantify differences of two corresponding protein samples To reflect the complexity of the intensity distributions more completely, additional orthogonal measures may complement the correlation analysis. A suitable orthogonal measure is for example the overall labeling of different protein samples that can be obtained by the integral of the intensity distribution, I. The significance of the detected differences can be demonstrated by using statistical ANOVA (analysis of variance) tests.

INDUSTRIAL APPLICATION OF THE INVENTION

The enzyme cascade amplification and detection of the present invention is particularly useful as a quality control instrument in the production of critical proteins or other bio-macromolecules, e.g., proteins used for diagnostics and therapy. It allows the validation of reproducibility in diverse biotechnological applications. The method is applicable to all bio-macromolecules, including proteins such as post-translationally modified proteins (e.g. glycosylated or phosphorylated proteins), or membrane proteins, as well as protein complexes.

In particular, the method allows for high-sensitivity detection of heterogeneities in even complex protein preparations with high accuracy. Protein structural changes may be analysed and small conformational differences may be detected directly in complex biological samples, such as in cell or blood extracts, on a large scale without the need for protein purification or enrichment.

The invention is particularly useful in the development and manufacturing of biopharmaceutical products to determine the differences between protein samples, for instance, when analysing the lot-to-lot variability between different product batches, during process characterization, to determine the impact of various process steps on the product (e.g. virus inactivation which uses a low pH) on the protein, or for comparisons between the reference biopharmaceutical product and the biosimilar as part of a biosimilarity exercise, which comprises an extensive structural characterization of both reference and biosimilar product.

Further, the method is useful for detecting and quantifying an aggregation behavior in protein samples. In particular, the A state of antibodies is known to exhibit an increased aggregation behavior as compared to native antibodies. The enzyme cascade is able to detect aggregation in protein samples, as exemplified herein by the comparison of the wild type and the A-state form of Rituximab.

Further, the method is useful for pattern recognition for deviations from typical treatments. A particular strength of the enzyme cascade is in serving as a pattern recognition system to different protein preparations. Lack of reproducibility of protein experiments is often related to slight variations in the preparation process, which may, however, have a critical impact on the protein quality. Typical variations in a protein preparation can include, for example, (i) exposure to room temperature; (ii) freeze and thaw cycles; (iii) exposure to sun light. The effects of these parameters may vary with the particular protein of interest and are often underestimated. For example, the effect of sun light on protein preparations can be mimicked by short UV exposures, which have a strong detrimental effect on the protein. These effects can then be analyzed and quantified by performing the enzyme cascade treatment of the present invention as described above. Similar as for the extended sun light exposure, the enzyme cascade can be exploited as a characteristic pattern recognition system for a series of typical preparations.

EXAMPLES

The method of the present invention will further be described by way of the following non-limiting examples, which use Rituximab, a chimeric monoclonal antibody directed against the protein CD20, as model protein for demonstrating the method according to the present invention.

General Description of Experimental Procedure

Protein (of interest, POI) is buffer exchanged and adjusted to a defined concentration, preferentially into the range of 0.1-50 mg/ml, more preferentially in the range of 0.5-2 mg/ml; reaction conditions: disfavored are buffers with calcium chelating activity (e.g., citrate, phosphate), or with amine functions (e.g., Tris), preferred are buffers such as Na acetate at concentrations from 50-500 mM, preferentially 100-200 mM with a pH matching the pH optimum of the used enzymes and the stability of the test protein; addition of modifying enzyme at a molar ratio in the range of modifying enzyme:POI of 10:1 to 1:1000, preferentially in the range of 1:3 to 1:100; temperature in the range from 4° C. to 40° C., preferentially at 37° C.; incubation time in the range from 1 min to 72 h, preferentially 30 min to 5 h, depending on the respective enzyme; stop of the reaction by addition of a specific inhibitor targeting exclusively the used enzyme; addition of second modifying enzyme, incubation; stop; etc. preferred readout of reaction (e.g. western blot, MS, etc.).

Figure 2:
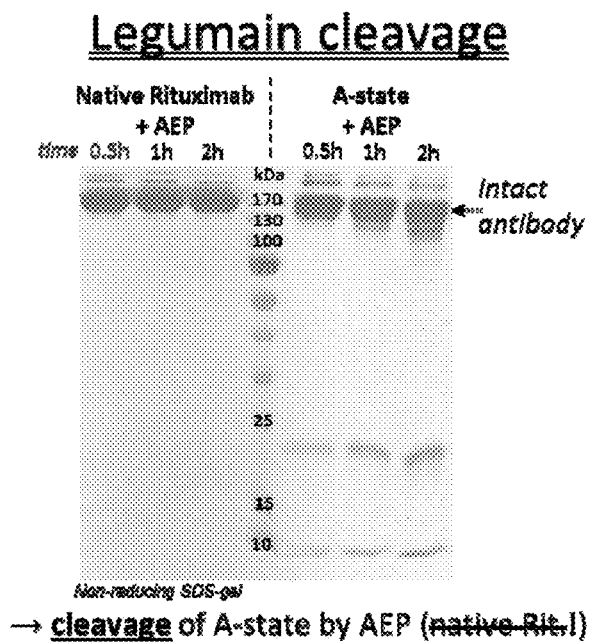
FIG. 2: Distinction of Rituximab native state and A-state by limited proteolysis (AEP).

Comparative Example 1 (FIG. 2)

According to the following protocol, native Rituximab and Rituximab A-state (a stable alternative conformation of an antibody induced by acidic pH treatment) were differentiated via a single enzymatic treatment (proteolytic cleavage) with legumain (AEP).

Sample Preparation

Before enzymatic treatment with AEP, a sample of native (non-treated) Rituximab (=sample 1) was buffer-exchanged into 100 mM Sodium acetate pH 4.5, 20 mM NaCl by using a NAP-5™ column.

In order to compare native Rituximab vs. Rituximab A-state, a sample of Rituximab was buffered to pH 2.2 by adding a defined amount of 2 M Malonic acid pH 0.97 (=sample 2, A-state). After 20', sample 2 was rebuffered into 20 mM citric acid pH 4.0, 20 mM NaCl (NAP-5™ column).

Both samples were adjusted to a concentration of 0.5 mg/ml.

Enzymatic Treatment

To both samples AEP was added at a molar ratio of 1:35 (AEP:Rituximab). The reactions were incubated at 37° C. for 2 h.

Readout

Samples were taken (5 µg protein per SDS-PAGE sample) after 30', 1 h, and 2 h, mixed with non-reducing loading buffer and subjected to SDS-PAGE.

Result

Rituximab in its native conformation can be distinguished, although with poor resolution, from its A-state by a single enzymatic treatment with AEP. In contrast to native Rituximab, for Rituximab A-state two distinct bands are visible on the SDS-PAGE, indicating at least 2 cleavage events which do not happen for native Rituximab.

Figure 3:
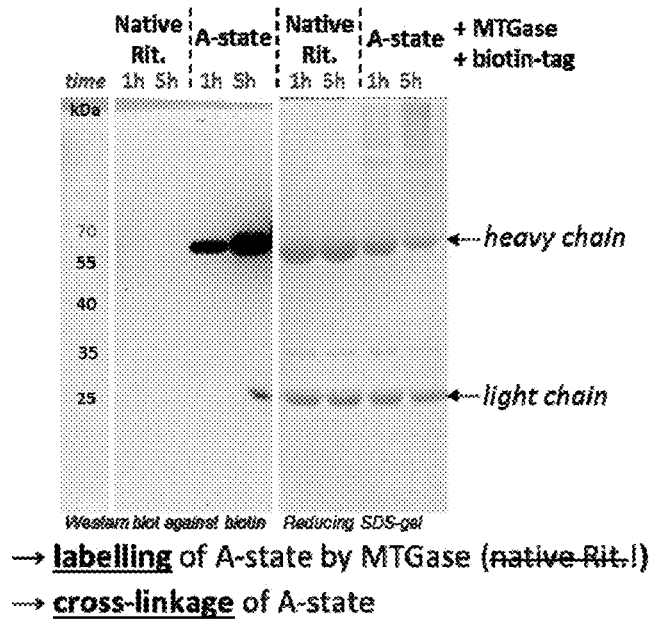
FIG. 3: Distinction of Rituximab native state and A-state by transglutamination (mTGase).

Comparative Example 2 (FIG. 3)

According to the following protocol, native Rituximab and Rituximab A-state were differentiated via a single enzymatic treatment (transglutamination) with microbial transglutaminase (MTGase).

Sample Preparation

Analogous to the experiment of Comparative Example 1, native Rituximab (sample 1) and a sample of Rituximab A-state (sample 2) were buffer exchanged into 20 mM citric acid pH 4.0, 20 mM NaCl. The concentration of both samples was adjusted to 0.5 mg/ml.

Enzymatic Treatment

To both samples mTGase was added at a molar ratio of 1:20 (mTGase:Rituximab). Additionally, a biotinylated glutamine-donor peptide (Z-Gln-Gly-CAD-Biotin) was added for subsequent transglutaminase catalyzed labelling of Rituximab at a molar ratio of 1:100 (Rituximab:peptide). The reactions were incubated at 37° C. for 5 h.

Readout

Samples were taken (5 µg protein per SDS-PAGE sample) after 1 h and 5 h, mixed with reducing loading buffer and subjected to SDS-PAGE and western blotting (using Streptavidin Poly-HRP for chemiluminescent western blot detection).

Result

Rituximab in its native conformation can be distinguished from its A-state by a single enzymatic treatment with mTGase. In contrast to native Rituximab, Rituximab A-state is labelled by mTGase with the used Z-Gln-Gly-CAD-Biotin peptide (signal on western blot for A-state, but not for native Rituximab). Additionally, Rituximab A-state is crosslinked into insoluble polymers by mTGase ("smear" on upper part of corresponding SDS-gel), which is not the case for native Rituximab.

Figure 4:
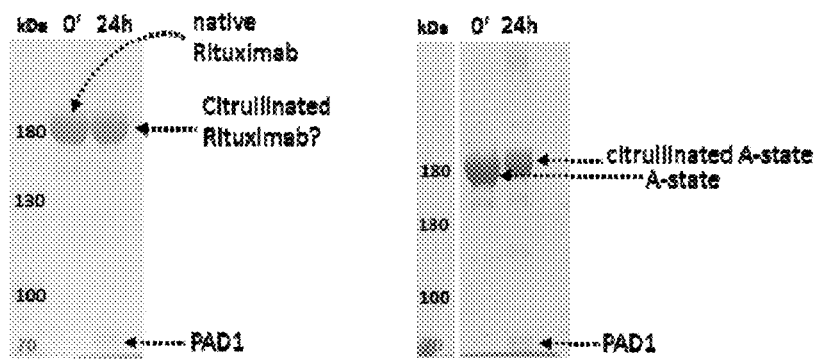
FIG. 4: Distinction of Rituximab native state and A-state by citrullination (PAD1).

Comparative Example 3 (FIG. 4)

According to the following protocol, native Rituximab and Rituximab A-state were differentiated via a single enzymatic treatment (citrullination) with peptidylarginine deiminase 1 (PAD1).

Sample Preparation

Similar to the experiments of Comparative Examples 1 and 2, native Rituximab (sample 1) and a sample of Rituximab A-state (sample 2) were buffer exchanged into 50 mM sodium acetate pH 4.5, 20 mM NaCl, 5 mM $CaCl_2$. The concentration of both samples was adjusted to 0.6 mg/ml.

Enzymatic Treatment

To both samples PAD1 was added at a molar ratio of 1:5 (PAD1:Rituximab). The reactions were incubated at 37° C. for 24 h.

Readout

Samples were taken (5 μg protein per SDS-PAGE sample) before PAD1 addition (0') and after 24 h, mixed with non-reducing loading buffer and subjected to SDS-PAGE.

Result

Several citrullinated proteins have been found to display an apparent increase in molecular weight on SDS-PAGE (due to citrullination-induced unfolding of the citrullinated protein). Same can be observed for Rituximab A-state after 24 h of citrullination, but not for native Rituximab. Although this does not necessarily indicate that native Rituximab is not citrullinated at all, it presumably demonstrates less citrullination/citrullination at different sites than for Rituximab A-state.

FIGS. 2-4 demonstrate differentiation between structural variants of proteins by using single enzymatic modifications.

Figure 5:
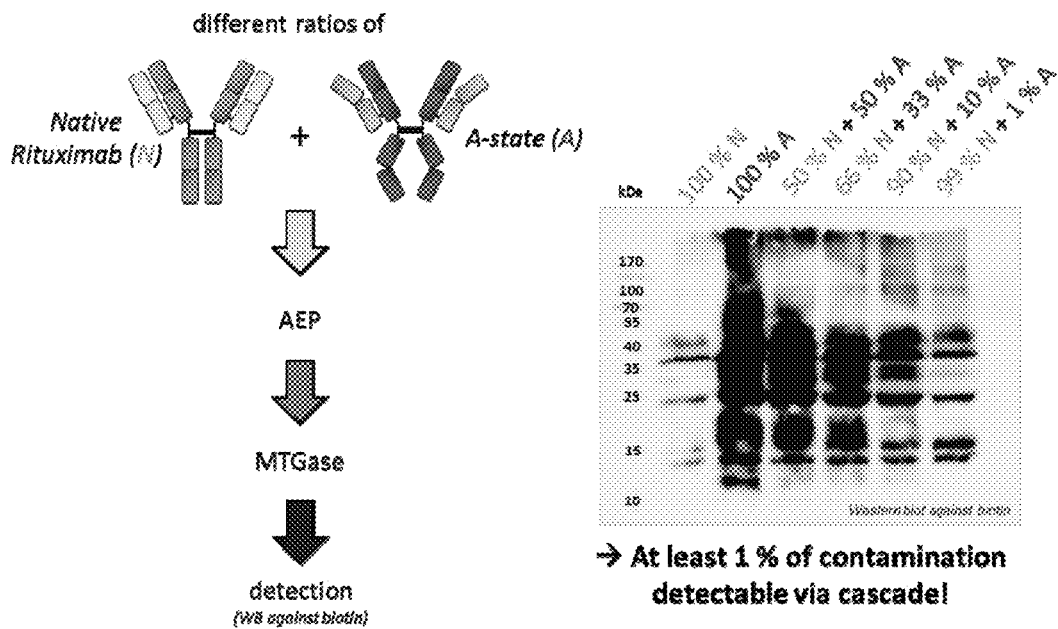
FIG. 5: Distinction of Rituximab native state and A-state by two-step cascade treatment (limited proteolysis followed transglutamination, detection with biotin immunolabelling).

Example 1 (FIG. 5)

Comparison of Native Rituximab Vs. Rituximab A-State Via a 2-Step Cascade Treatment For this experiment different samples containing distinct amounts of native Rituximab ("N") and Rituximab A-state ("A") were prepared and subjected to a 2-step enzyme cascade treatment. According to the following protocol, native Rituximab and Rituximab A-state were differentiated via a 2-step enzyme cascade treatment involving (1) protease cleavage by legumain (AEP) and (2) transglutamination by mTGase.

Sample Preparation

Similar to the experiments of Comparative Examples 1 to 3 native Rituximab and a sample of Rituximab A-state were buffer exchanged into 20 mM citric acid pH 4.0, 20 mM NaCl. The concentration of both samples was adjusted to 1.64 mg/ml.

For this experiment different samples containing distinct amounts of native Rituximab ("N") and Rituximab A-state ("A") were prepared by mixing defined amounts of native Rituximab and Rituximab A-state:

1: 100% native Rituximab
2: 100% A-state
3: 50% native Rituximab+50% A-state
4: 66% native Rituximab+33% A-state
5: 90% native Rituximab+10% A-state
6: 99% native Rituximab+1% A-state Enzymatic Treatment Step 1: Proteolytic Cleavage by AEP To all of the six samples (1-6) AEP was added at a molar ratio of 1:100 (AEP:Rituximab). The reactions were incubated at 37° C. for 2 h. After 2 h, proteolysis was stopped via addition of a specific inhibitor targeting AEP (YVAD-cmk).

Step 2: Transglutamination by mTGase

After proteolytic cleavage by AEP, to each of the six samples mTGase was added at a molar ratio of 1:3 (mTGase:Rituximab).

Additionally, a biotinylated glutamine-donor peptide (Z-Gln-Gly-CAD-Biotin) was added for subsequent transglutaminase catalyzed labelling of Rituximab at a molar ratio of 1:200 (Rituximab:peptide). The reactions were incubated at 37° C. for 4 h.

Readout

Samples were taken (20 μg protein per SDS-PAGE sample), mixed with reducing loading buffer and subjected to SDS-PAGE and western blotting (using Streptavidin Poly-HRP for chemiluminescent western blot detection).

Result

As clearly shown in FIG. 5, this experiment demonstrates 2-step cascade-mediated signal amplification. Due to this experiment, the sensitivity of such enzyme cascades was shown to be at least 1%, i.e. it was shown to be possible to detect at least 1% of "contamination", i.e. 1% of Rituximab A-state in a sample of 99% natively folded Rituximab.

Figure 6:
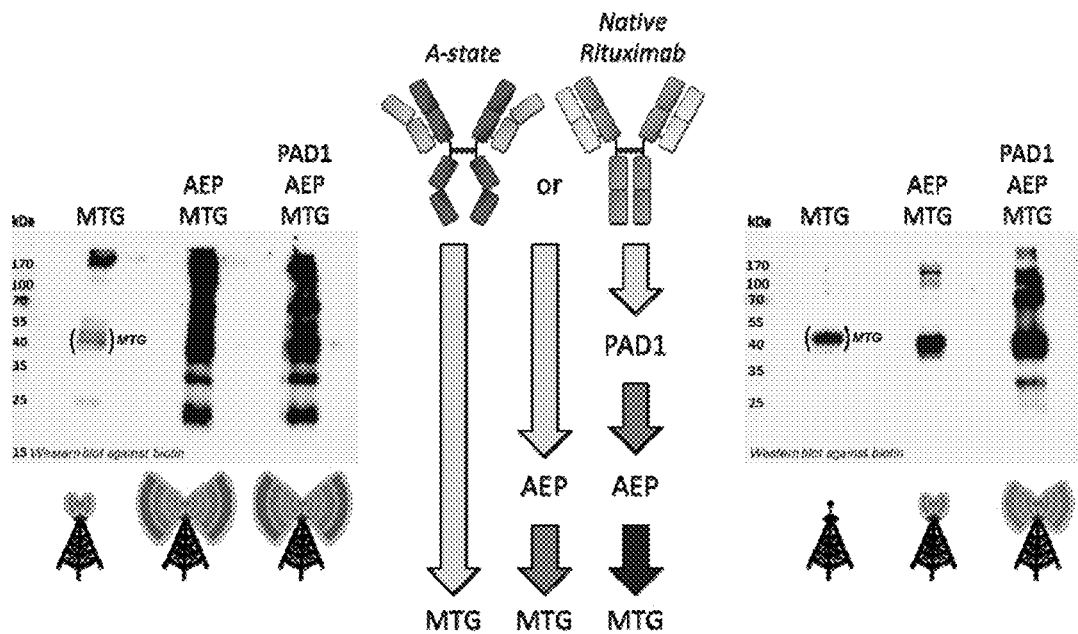
FIG. 6: Signal amplification by citrullination followed by limited proteolysis and transglutamination (triple cascade), detection by biotin-immunoblotting.

Example 2 (FIG. 6)

Comparison of Native Rituximab Vs. Rituximab A-State Via a 3-Step Cascade Treatment According to the following protocol, native Rituximab and Rituximab A-state were used to demonstrate the potential of enzyme cascades to amplify signals (depending on cascade depth).

Sample Preparation

Similar to the experiments of Example 1 native Rituximab (sample 1) and a sample of Rituximab A-state (sample 2) were buffer exchanged into 50 mM sodium acetate pH 4.5, 20 mM NaCl, 5 mM $CaCl_2$. The concentration of both samples was adjusted to 0.6 mg/ml.

For both native Rituximab and Rituximab A-state, three samples of each were prepared which were subjected to either a single enzymatic treatment (A) or to different enzyme cascades involving two or three enzymes (B and C):

A: $1^{st}$ transglutamination by mTGase
B: $1^{st}$ proteolytic cleavage by AEP & $2^{nd}$ transglutamination by mTGase
C: $1^{st}$ Citrullination by PAD1, $2^{nd}$ proteolytic cleavage by AEP, & $3^{rd}$ transglutamination by mTGase To ensure that signal amplification resulted from the introduction of an additional enzyme into the enzyme cascades, and not from length of incubation, addition of a buffer substance, addition of an inhibitor, etc, all reactions (native Rit/A-state, 3 samples each (samples 1A-C, samples 2A-C)) were treated equally, except for the omission/addition of the respective enzyme(s).

Enzymatic Treatment

Step 1: Citrullination in Samples 1C and 2C

To samples 1C and 2C PAD1 was added at a molar ratio of 1:5 (PAD1:Rituximab). To samples 1A,B and samples 2A,B an equal amount of PAD1-buffer was added (no enzyme, only the buffer in which the respective enzyme was present).

All reactions were incubated at 37° C. for 36 h.

To all of the six reactions 10 mM EDTA was added in order to inhibit further PAD1 activity, at least in samples 1C and 2C, all other reactions (1A,B and 2A,B) did not contain PAD1; nevertheless EDTA was equally added to 1A,B and 2A,B.

Step 2: Proteolytic Cleavage by AEP in Samples 1B,C and 2B,C

To samples 1B,C and 2B,C AEP was added at a molar ratio of 1:50 (AEP:Rituximab). To samples 1A and 2A an equal amount of AEP-buffer was added. All reactions were incubated at 37° C. for 15'.

To all of the six reactions a specific AEP inhibitor was added (YVAD-cmk).

Step 3: Transglutamination in Samples 1A,B,C and 2A,B,C To all samples (1A-C, 2A-C) mTGase was added at a molar ratio of 1:3 (Rituximab:mTGase).

Additionally, a biotinylated glutamine-donor peptide (Z-Gln-Gly-CAD-Biotin) was added for subsequent transglutaminase catalyzed labelling of Rituximab at a molar ratio of 1:400 (Rituximab:peptide).

The reactions were incubated at 37° C. for 5 h.

Readout

Samples were taken (5 µg protein per SDS-PAGE sample), mixed with non-reducing loading buffer and subjected to SDS-PAGE and western blotting (using Streptavidin Poly-HRP for chemiluminescent western blot detection).

Result

The western blot on the left side of FIG. 6 shows the signals obtained for samples 2A-C (Rituximab A-state). Strong signal amplification from 2A to 2B is apparent; there is almost no room for further signal amplification from 2B to 2C.

The western blot on the right side of FIG. 6 shows the signals obtained for samples 1A-C (native Rituximab). Each additional step in the cascades amplifies the initially very low signal.

Figure 7:
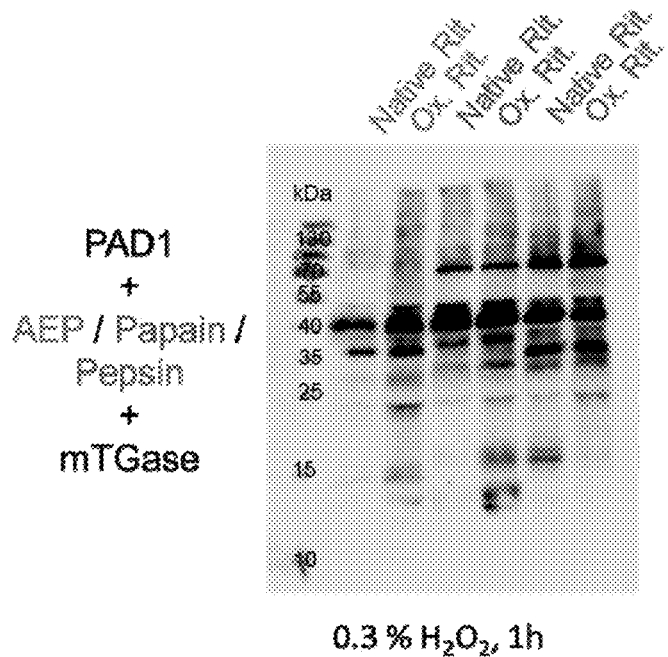
FIG. 7: Distinction of native Rituximab from oxidized Rituximab by a triple cascade treatment.

Example 3 (FIG. 7)

Comparison of Native Rituximab Vs. Oxidized Rituximab Via a 3-Step Cascade Treatment According to the following protocol, oxidized and non-oxidized Rituximab were differentiated via a 3-step cascade treatment involving (1) citrullination by PAD1, (2) protease cleavage by legumain, papain, or pepsin, and (3) transglutamination by mTGase.

Sample Preparation

Before cascade-treatment, a sample of native (non-treated) Rituximab (=sample 1) was buffer-exchanged into 100 mM Sodium acetate pH 4.5, 20 mM NaCl, 5 mM $CaCl_2$ (by using a NAP-5™ column).

In order to compare native vs. oxidized Rituximab, a sample of Rituximab was oxidized (=sample 2) via addition of 0.3% $H_2O_2$ for one hour. The $H_2O_2$ was removed by rebuffering into 100 mM Sodium acetate pH 4.5, 20 mM NaCl, 5 mM $CaCl_2$. Both samples were adjusted to a concentration of 0.6 mg/ml.

Step 1: Citrullination by PAD1

To both samples PAD1 was added at a ratio of 1:5 (PAD1:Rituximab). The reactions were incubated at 37° C. for 65 h.

Citrullination was stopped via addition of 10 mM EDTA (to remove calcium, which is essential for PAD1 activity).

Step 2: Protease Cleavage by AEP/Papain/Pepsin

After citrullination, samples 1 and 2 were trisected in order to be able to subject the samples to three different proteases, namely legumain (AEP), papain, or pepsin.

The respective proteases were added at a ratio of 1:50 (protease:Rituximab). The reactions were incubated at 37° C. for 2.5 h.

Proteolysis was stopped via addition of specific inhibitors targeting the used protease (YVAD-cmk for AEP, E64 for Papain, Pepstatin A for Pepsin).

Step 3: Transglutamination by mTGase

After citrullination and proteolytic cleavage, to each of the six samples (1a: native Rituximab, citrullinated and AEP-cleaved; 1b: nat. Rituximab, citrullinated and papain-cleaved; 1c: nat. Rituximab, citrullinated and pepsin-cleaved; 2a: oxidized Rituximab, citrullinated and AEP-cleaved; 2b: ox. Rituximab, citrullinated and papain-cleaved; 2c: ox. Rituximab, citrullinated and pepsin-cleaved) mTGase was added at a ratio of 1:3 (mTGase:Rituximab).

Additionally, a biotinylated glutamine-donor peptide (Z-Gln-Gly-CAD-Biotin) was added for subsequent transglutaminase catalyzed labelling of Rituximab at a ratio of 1:400 (Rituximab:peptide). The reactions were incubated at 37° C. for 5 h.

Readout

Samples were taken (5 µg protein per SDS-PAGE sample), mixed with reducing loading buffer and subjected to SDS-PAGE and western blotting (using Streptavidin Poly-HRP for chemiluminescent western blot detection).

Result

As clearly shown in FIG. 7, native Rituximab can be easily distinguished from oxidized Rituximab by all of the three applied cascades, since the obtained signals for the two samples differ in each case.

Figure 8:
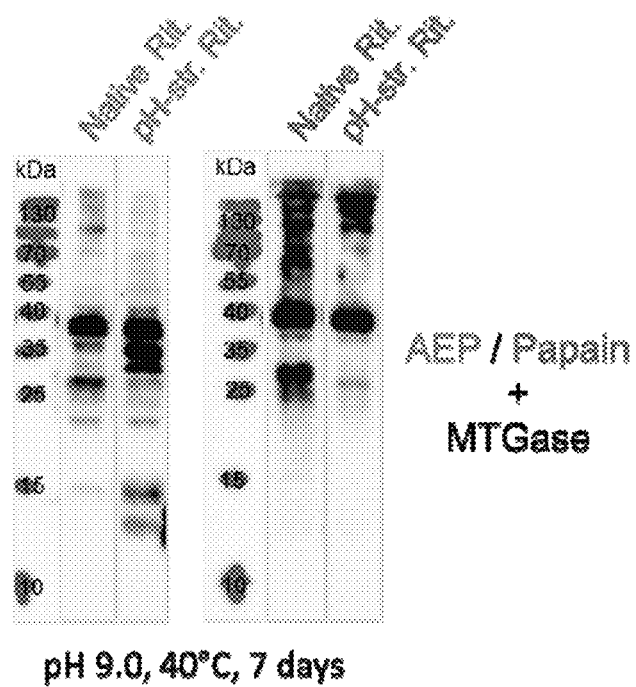
FIG. 8: Distinction of native Rituximab from basic pH-stressed Rituximab by a two-step cascade treatment.

Example 4 (FIG. 8)

Comparison of Native Vs. Basic pH-Stressed Rituximab (pH 9)

One Rituximab sample was pH-stressed by incubating in 25 mM Tris pH 9.0 for 7 days at 40° C. and subsequently re-buffered into 100 mM Na acetate pH 4.5, 20 mM NaCl using NAP-5™ columns ("basic pH-stressed Rituximab"). According to the experimental procedures described in Example 1 native vs. basic pH-stressed Rituximab were differentiated via a 2-step cascade treatment involving (1) protease cleavage by legumain or papain and (2) transglutamination by mTGase.

Result

As clearly shown in FIG. 8, native Rituximab can be easily distinguished from basic pH-stressed Rituximab by the two applied cascades, since the obtained signals for the two samples differ in each case.

Figure 9:
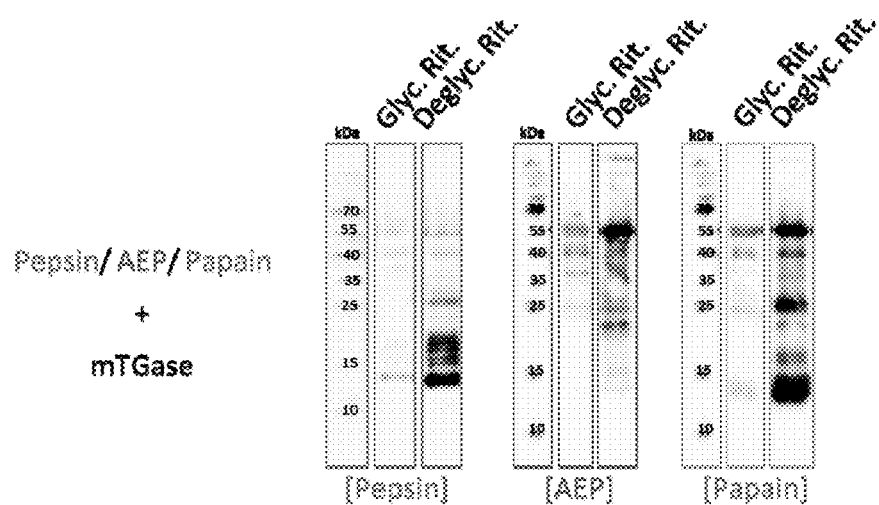
FIG. 9: Distinction of glycosylated Rituximab from deglycosylated Rituximab by a 2-step cascade treatment.

Example 5 (FIG. 9)

Comparison of Glycosylated Vs. Deglycosylated Rituximab

One Rituximab sample was deglycosylated by incubating in 50 mM sodium phosphate buffer pH 7.5, with 500 units of PNGase F for 20 hours at 37° C. and subsequently re-buffered into 100 mM Na acetate pH 4.5, 20 mM NaCl using NAP-5™ columns ("deglycosylated Rituximab"). According to the experimental procedures described in Example 1, glycosylated vs. deglycosylated Rituximab were differentiated via a 2-step cascade treatment involving (1) protease cleavage by legumain, papain, or pepsin, and (2) transglutamination by mTGase.

Result

As clearly shown in FIG. 9, glycosylated Rituximab can be easily distinguished from deglycosylated Rituximab by all of the three applied cascades, since the obtained signals for the two samples differ in each case.

Figure 10:
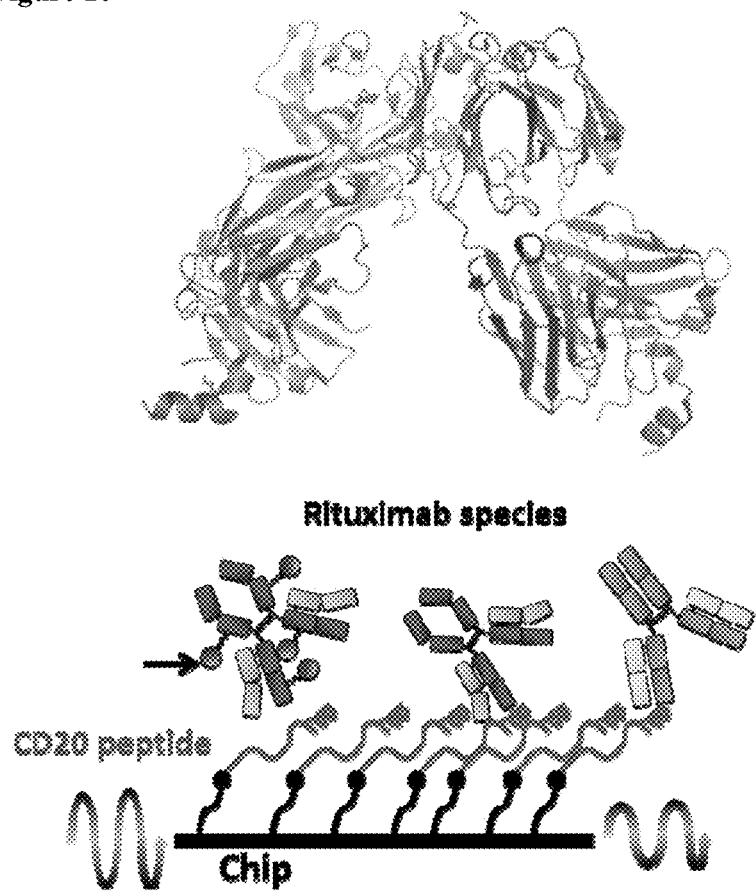
FIG. 10: Quantitative detection of the amplified signal by binding kinetics analysis (SAW method).

Example 6 (FIG. 10)

Enzyme cascade treatment is carried out as described in Example 1, whereas signal detection is performed as follows.

The CD20 peptide (NIYNCEPANPSEKNSPSTQYCYSIQ) or its K-R variant (NIYNCEPANPSERNSPSTQYCYSIQ) are immobilized to a biosensor ("SAW") chip by amine coupling. Enzymatically modified Rituximab is flushed over the chip at different concentrations, reflecting the expected Kd values of binding. The binding of Rituximab onto the chip will induce a phase change in the acoustic wave traversing the CD20-loaded chip, which allows determining the binding affinity of Rituximab to the chip. Signal detection by using an SAW chip is schematically demonstrated in FIG. 10.

Figure 11:
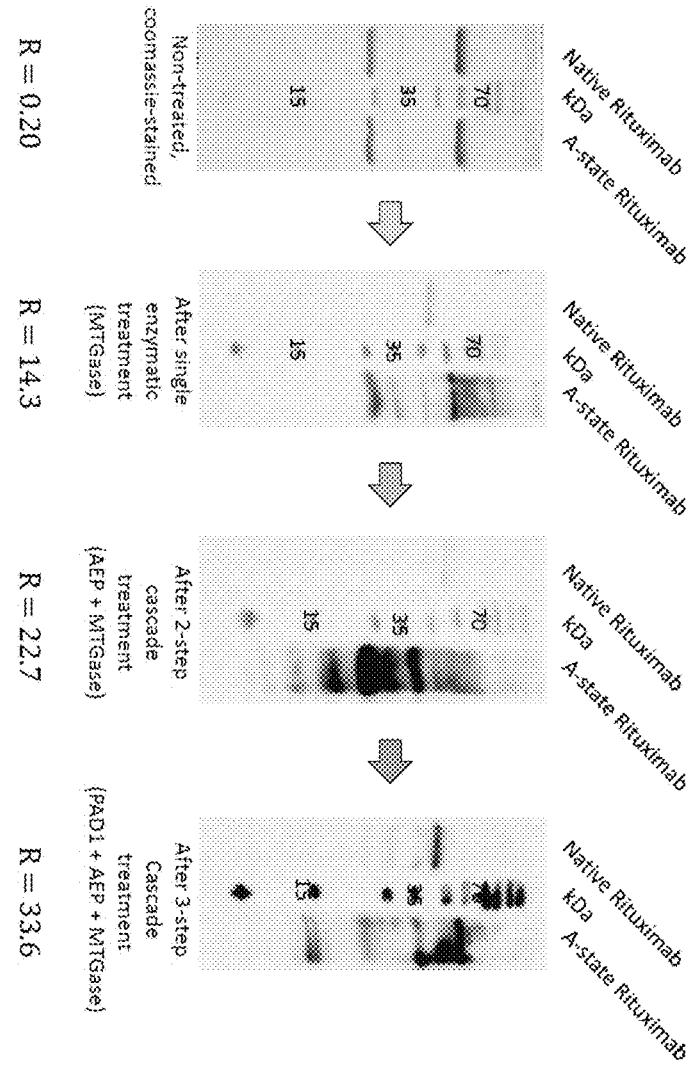
FIGS. 11 and 12: Quantification of signal amplification by immunoblot staining and determination of relative differences and/or the Pearson's correlation product.
Figure 12:
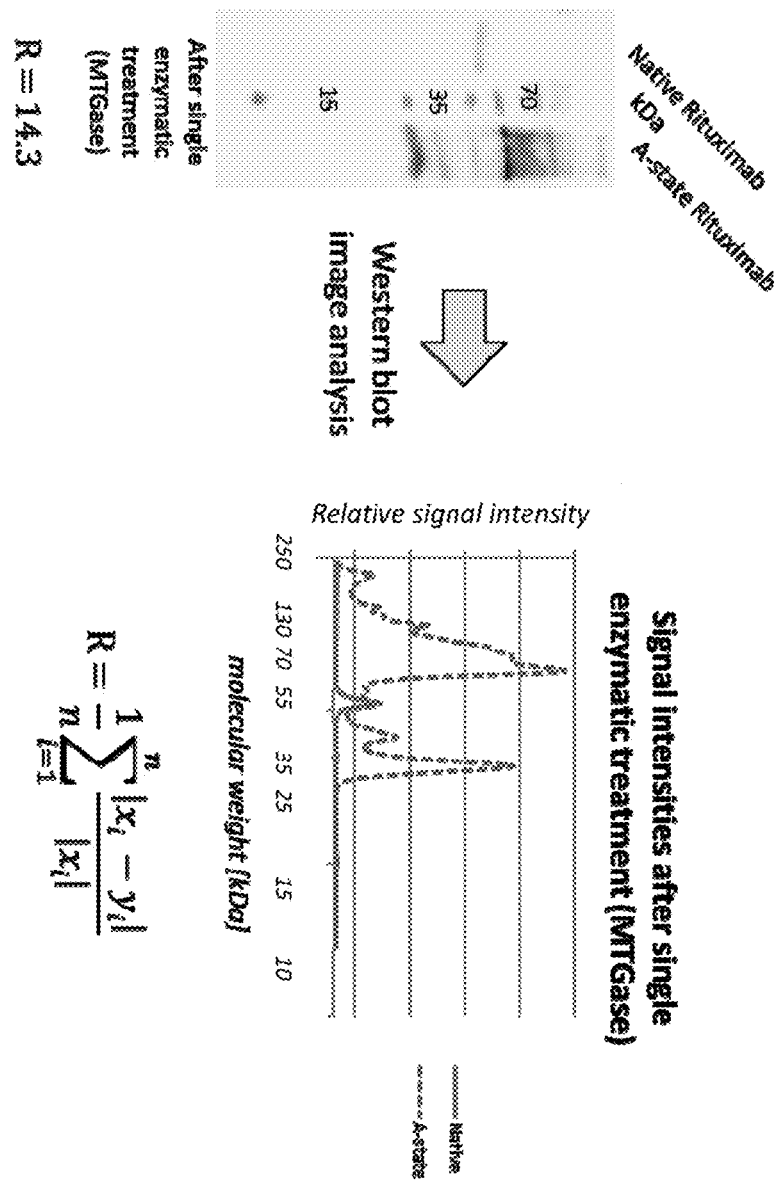

Example 7 (FIGS. 11 and 12)

Comparison of native Rituximab vs. Rituximab A-state was performed via a 3-step cascade treatment similar to the method described in Example 2, but wherein the following conditions have been used:
1) Citrullination by PAD 1; ratio 1:5 (PAD1:Rituximab); 22 h, 37° C.
2) Protease digest by AEP; ratio 1:50 (AEP:Rituximab); 2.5 h, 37° C.
3) Labelling by MTGase; ratio 1:5 (Rituximab:MTGase); 3 h, 37° C.

The protein samples were analyzed by Western blotting. The corresponding intensity distributions are then plotted as a function of molecular weight. Average relative differences were determined by comparing the signal intensities of the native state of Rituximab with the A-state of Rituximab.

As can be seen in FIGS. 11 and 12, the differences between the protein samples could be enhanced after each enzyme treatment, as visualized by the signal intensities and quantitatively determined by the average relative difference.

The invention claimed is:

1. A method for identification of conformational differences between a first and a second protein, the method comprising the steps of:
a) providing a first protein sample comprising at least a first protein,
b) providing at least a second protein sample comprising at least a second protein having substantially the same amino acid sequence as the first protein but being different from the first protein,
c) subjecting the at least first and second protein samples to enzymatic modification with a first enzyme having a different binding affinity and/or catalytic turnover of the at least first and second protein,
d) repeating step c) one or more times with a second or further enzyme, wherein each enzymatic modification step amplifies differences between the first and the second protein,
e) visualizing differences between the first and second protein, wherein the visualizing is performed by one or more of polyacrylamide gel electrophoresis (PAGE), Western Blot, enzyme-linked immunosorbent assay (ELISA), high performance liquid chromatography (HPLC) and Mass spectrometry, capillary electrophoreses, Fourier-Transform infrared spectroscopy, circular dichroism, dynamic light scattering (DLS), thermal shift assay, nuclear magnetic resonance (NMR), X-ray, chromatography, and fluorescence spectroscopy, and
f) identifying conformational differences between the first and the second protein based on visualized differences between the first and the second protein,
wherein the first, second or further enzyme is selected from cyclases, phosphatases, kinases, methyl transferases, ligases proteases, oxidases, hydroxylases, reductases, isomerases, ubiquitinases, acetylases, transglutaminases and deiminases.

2. The method according to claim 1, wherein each enzyme is different from any enzyme in the one or more preceding enzymatic modification steps.

3. The method according to claim 1, the method comprising three or more different enzymatic modification steps.

4. The method according to claim 1, wherein the first and second proteins are identical in the encoded amino acid sequence and have different conformational structures.

5. The method according to claim 1, wherein the first and second protein differ from each other by one or more of the state of gylcosylation, oxidation and disulfide bond formation.

6. The method according to claim 1, wherein enzymatic modification is performed by one or more of (de-)phosphorylation, (de-)glycosylation, disulfide formation, oxidation, (de-)amidation, (de-)imination, (de-)methylation, transglutamination, limited proteolysis, lysine cross-linkage, hydroxylation, acetylation, racemization, ubiquination, and pyroglutamate formation.

7. The method according to claim 6, wherein enzymatic modification is performed by two or more of citrullination, transglutamination and limited proteolysis.

8. The method according to claim 7, wherein enzymatic modification is performed by citrullination, transglutamination and proteolysis.

9. The method according to claim 1, wherein the protease is selected from legumain, thrombin, factor Xa, papain, or pepsin.

10. The method according to claim 1, wherein the final enzymatic modification step comprises the step of labelling the protein with a chemiluminescent or fluorescent label.

11. The method according to claim 1, wherein the first enzyme is peptidyl arginine deiminase, the second enzyme is a protease and the third enzyme is microbial transglutaminase.

12. The method according to claim 1, wherein the first enzyme is a protease, the second enzyme is a peptidyl arginine deiminase and a third enzyme is microbial transglutaminase.

* * * * *